United States Patent [19]

Röhrscheid

[11] Patent Number: 5,300,717
[45] Date of Patent: Apr. 5, 1994

[54] PROCESS FOR THE PREPARATION OF DIXYLYLPROPANE

[75] Inventor: Freimund Röhrscheid, Kelkheim/Taunus, Fed. Rep. of Germany

[73] Assignee: Hoechst Aktiengesellschaft, Frankfurt am Main, Fed. Rep. of Germany

[21] Appl. No.: 44,584

[22] Filed: Apr. 8, 1993

[30] Foreign Application Priority Data

Apr. 10, 1992 [DE] Fed. Rep. of Germany ....... 4212055

[51] Int. Cl.⁵ .......................... C07C 2/00; C07C 2/68; C07C 2/70
[52] U.S. Cl. .................................. 585/320; 585/310; 585/321; 585/465; 585/466; 585/440
[58] Field of Search ............... 585/320, 310, 321, 323, 585/440, 465, 466

[56] References Cited

U.S. PATENT DOCUMENTS 2,578,207 12/1951 Pines et al. .......................... 585/320
2,712,543 7/1955 Gresham et al. .
4,649,207 3/1987 Lau et al. .............................. 585/320

*Primary Examiner*—Asok Pal

[57] ABSTRACT

In a multi-step process, dixylylpropane is obtained inter alia via the hitherto unknown 1,2-dimethyl-4-(α-chloroisopropyl)benzene, the readily accessible compounds o-xylene and propene being employed as starting compounds. The process yields the desired compound in high yield and isomer purity and is distinguished by a small amount of by-products. It is therefore particularly suitable for further processing without problems. The process involves the sequence of (a) Friedel-Crafts alkylation of ortho-xylene with propylene, (b) dehydrogenation of the isoproplyxlene into isopropenylxylene, (c) which is then hydrochlorinated into chloroisopropylxylene, (d) and then alkylated with a second ortho-xylene modecule to obtain the final product dixylylpropane.

14 Claims, No Drawings

PROCESS FOR THE PREPARATION OF DIXYLYLPROPANE

The invention relates to a process for the preparation of dixylylpropane.

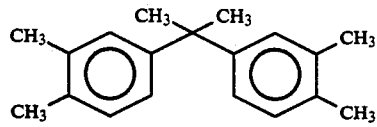

Dixylylpropane, also called 2,2-bis(3,4-dimethylphenyl)propane, is, for example, an intermediate for the preparation of isopropylidenebisphthalic anhydride. The latter compound is a component for thermoplastically processable polyimides. The preparation of dixylylpropane from o-xylene and 2,2-dichloropropane has already been described (U.S. Pat. No. 2,712,543). The 2,2-dichloropropane required is, however, only accessible with difficulty.

The object was therefore to find a novel synthesis which starts from easily accessible chemicals and which yields the desired substance in high yield.

The invention therefore relates to a process for the preparation of dixylylpropane from o-xylene and propene, in which, stepwise a) o-xylene is reacted with propene to give 1,2-dimethyl-4-isopropylbenzene, b) 1,2-dimethyl-4-isopropylbenzene is catalytically dehydrogenated to give 1,2-dimethyl-4-isopropenylbenzene, c) 1,2-dimethyl-4-isopropenylbenzene is reacted with hydrogen chloride to give 1,2-dimethyl-4-(α-chloroisopropyl)benzene and finally d) 1,2-dimethyl-4-(α-chloroisopropyl)benzene is condensed with o-xylene to give dixylylpropane.

The process can be represented schematically as follows:

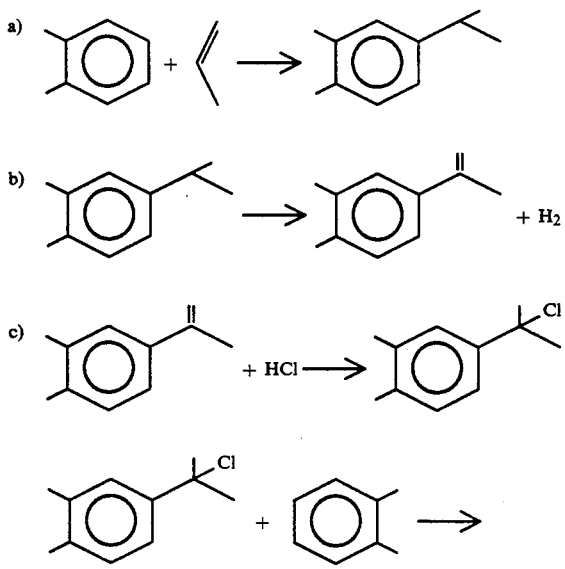

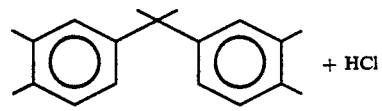

The claimed process for the preparation of dixylylpropane utilizes the readily accessible compounds o-xylene and propene as starting compounds, yields the desired compound in high yield and isomer purity and is distinguished by a low yield of by-products. It is thus very highly suitable for further processing without problems.

The procedures of the individual steps are known per se. Thus, the isopropylation of the o-xylene in step a) is carried out by introduction of propene into a mixture of o-xylene in the presence of a catalyst. In this process, the catalyst should have only a mildly alkylating effect and must not rearrange the methyl groups or react itself with the aromatic components even at relatively high temperature.

To date, two types of catalysts for the reaction of step a) have been described in the literature which satisfy these demands. A catalyst of this type is $BF_3$—$H_3PO_4$ (A. V.Topchiev et al., Dokl. Akad. Nauk SSSR, Vol. 134 (1960), pp. 844–847, English translation: pp. 1101–1104). On use thereof, after isopropylation of o-xylene in the two-phase mixture, o-xylene, 1,2-dimethyl-3-isopropylbenzene, 1,2-dimethyl-4-isopropylbenzene, diisopropylxylenes and high-boiling components are present in the organic phase.

The best yields of 1,2-dimethyl-4-isopropylbenzene can only be achieved by a limited isopropylation of the o-xylene, i.e. stoichiometric amounts of the starting compounds are not employed. The reaction with limited conversion thus leads, relative to 1,2-dimethyl-4-isopropylbenzene prepared, to an increased catalyst requirement and increased expenditure during work-up.

The reaction of o-xylene with propene in the presence of $AlCl_3$—$CH_3NO_2$ as a catalyst is also known (I. G. Gakh. et al., Z. Org. Khim, 1 [1965] pp. 1626–1627; English translation: pp. 1646–1647). The main product obtained is 1,2-dimethyl-4-isopropylbenzene, but in addition also 1,3-dimethyl-5-isopropylbenzene and trimethylbenzenes as isomerization products. More detailed information about the carrying-out of the experiments—except for the reaction temperature—is not given in the publication. Reworking gave significantly differing values with respect to yield and composition of the mixture obtained.

Step a) of the present process according to the invention enables propene to be reacted with o-xylene near to the molar ratio of 1:1, the substances employed being converted nearly completely to 1,2-dimethyl-4-isopropylbenzene using the catalysts $BF_3 \cdot H_3PO_4$ and $AlCl_3 \cdot CH_3NO_2$. Propene and o-xylene are employed in a molar ratio of 0.8–2.0, preferably 0.8–1.0, in particular 0.95–0.98:1. The catalyst preferably used is $AlCl_3 \cdot CH_3NO_2$, which can be removed from the reaction mixture particularly easily. The catalyst constituent $AlCl_3$ can be employed in a ratio of 0.001–0.3 mol, preferably 0.003–0.05 mol, in particular 0.005–0.02 mol, per mol of o-xylene. The molar ratio of $CH_3NO_2$ can be from 1 to 10, preferably 2 to 4, per mol of $AlCl_3$.

The activity of the catalyst is increased by a small amount of hydrogen chloride.

An advantage is that the catalyst $AlCl_3 \cdot CH_3NO_2$ can be removed from the reaction solution by precipitation and filtering off without washing with water or another medium. Precipitation is carried out by adding finely divided alkali metal or alkaline earth metal acetates, preferably by the acetates of sodium, potassium and calcium.

The reaction of o-xylene with propene in the presence of the catalysts mentioned is carried out at temperatures of 60°–130° C., preferably at 80°–100° C., in the course of 2–10, preferably 3–8, in particular 4–6 hours. A variant of the process consists in carrying out the addition of the propene to the o-xylene at low temperatures from 0°–60° C., preferably 0°–40° C., in the first step and then raising the reaction mixture to the above-mentioned reaction temperatures. In these processes, the compounds 1,2-dimethyl-3-isopropylbenzene, 1,2-dimethyl-3,5-diisopropylbenzene and 1,2-dimethyl-3,4,6-triisopropylbenzene formed in addition to the 1,2-dimethyl-4-isopropylbenzene are almost completely comproportionated and isomerized to the desired 1,2-dimethyl-4-isopropylbenzene in two steps.

It is of particular interest in the process according to step a) that all the organic components can be reutilized. For instance, the nitromethane obtained in the distillative work-up of the reaction mixture and also o-xylene and the distillation residue can be transferred to the reaction vessel and subjected there again, after addition of further components, to the reaction for the preparation of 1,2-dimethyl-4-isopropylbenzene.

The dehydrogenation of the 1,2-dimethyl-4-isopropylbenzene in step b) is carried out by one of the known methods, such as are described, for example, in HoubenWeyl "Methoden der organischen Chemie", (Methods of Organic Chemistry), vol. 5/16, p. 376 ff or in U.S. Pat. No. 3,429,941. It is convenient to use a catalyst of the composition $Fe_2O_3$—KOH—$Cr_2O_3$.

A mixture of 1,2-dimethyl-4-isopropylbenzene and 1,2-dimethyl4-isopropenylbenzene, whose boiling points are close together, is formed in the dehydrogenation. As a result, a distillative separation at the low temperatures necessary (<90° C.) and the associated low pressure becomes difficult. As a result of this, said mixture is preferably subjected to the further reaction.

To do this, the low-boiling fractions of the dehydrogenation product are removed by distillation in step c) and the mixture of 1,2-dimethyl-4-isopropylbenzene and 1,2-dimethyl-4-isopropenylbenzene is converted into a mixture of 1,2-dimethyl-4-isopropylbenzene and 1,2-dimethyl-4-(α-chloroisopropyl)benzene at −30° to +40° C., preferably at −10° to +10° C., using dry hydrogen chloride. The 1,2-dimethyl-4-isopropylbenzene can be removed from this mixture by distillation under reduced pressure (44° C./2 mbar, 31° C./1 mbar). The 1,2-dimethyl-4-(α-chloroisopropyl)benzene is employed in the condensation reaction of step d).

In step d) the synthesis of 2,2-dixylylpropane is carried out by reaction of 1,2-dimethyl-4-(α-chloroisopropyl)-benzene and o-xylene with aluminum chloride by means of Friedel-Crafts catalysis at temperatures from −25° to +30° C., preferably at −20° to 0° C. Reaction of the mixture of 1,2-dimethyl-4-(α-chloroisopropyl)benzene and 1,2-dimethyl-4-isopropylbenzene obtained in step c) with o-xylene is particularly preferred, by means of which an easily separable mixture of nitromethane, o-xylene, 1,2-dimethyl-4-isopropylbenzene and dixylylpropane results. The working-up of the reaction solution is carried out in a non-aqueous medium analogously to step a).

As a result of the anhydrous work-up, the Friedel-Crafts synthesis becomes an inexpensive process without complicated washing and phase separations. After the condensation to give the dixylylpropane, the residual hydrogen chloride is carried out of the reaction mixture with $N_2$ and absorbed in $H_2O$. The degassed reaction solution is treated with alkali metal or alkaline earth metal acetates, preferably calcium acetate, particularly preferably $Ca(OAc)_2/Ca(OH)_2$. Precipitated Al-$(OAc)_2$ and $CaCl_2$ are filtered off.

The nitromethane which is carried out during a water wash can be recovered by distillation during the anhydrous work-up carried out, which marks the economical side of the process. Additionally, no contamination of the water by $CH_3NO_2$ takes place.

EXAMPLES

1a) Isopropylation of o-xylene (temperature conditions according to the prior art)

6.37 kg of o-xylene and 0.165 kg of nitromethane were poured into a 10 l flask with a stirrer and gas inlet tube. 0.12 kg of anhydrous aluminum chloride were added at 20° C. with stirring. First, 5 g of hydrogen chloride and then, in the course of 2 hours, 2.02 kg of propene were passed in. The temperature was kept at 40° C. by cooling. At the end of the reaction the reaction mixture had the following composition: 1.4% nitromethane, 29.4% o-xylene, 23.0% 1,2-dimethyl-4-isopropylbenzene, 14.7% 1,2-dimethyl-3-isopropylbenzene, 24.5% 1,2-dimethyl-3,5-diisopropylbenzene, 8.3% 1,2-dimethyl-3,4,6-triisopropylbenzene.

1b) Comproportionation and isomerization to give 1,2-dimethyl-4-isopropylbenzene The batch according to Example 1a) was heated to 90° C. and kept at this temperature for 8 hours. At the end, the reaction mixture had the following composition: 1.4% nitromethane, 15.9% o-xylene, 77.2% 1,2-dimethyl-4-isopropylbenzene, 1.8% 1,2-dimethyl-3-isopropylbenzene, 3.5% 1,2-dimethyl-3,5-diisopropylbenzene, 0.2% residue, not determined.

1c) Precipitation of the catalyst 0.25 kg of calcium acetate×½ $H_2O$ was introduced in the hot state into the batch according to Example 1b), the mixture was stirred for 2 hours at 90° C. and then cooled, and the suspension was filtered with suction through a suction filter. The filter cake was washed twice with 0.15 kg of o-xylene each time.

About 8.3 kg of filtrate and 0.37 kg of metal salts (dry) are obtained. The filtrate contained no chlorine ions.

1d) Distillation of the filtrate from Example 1c) The filtrate could be distilled immediately in a column without further pretreatment.

At 1 bar, first 0.98 kg of a mixture of nitromethane (11%) and o-xylene were removed by distillation. This was followed by a fractional distillation at 300 mbar. After a forerun of 0.12 kg of a mixture of o-xylene and 1,2-dimethyl-4-isopropylbenzene, 6.05 kg of 1,2-dimethyl-4-isopropylbenzene were obtained at 155° ±0.5° C. The distillation residue (1.16 kg) consisted of 38% (0.44 kg) of 1,2-dimethyl-4-isopropylbenzene, 23% (0.27 kg) of 1,2-dimethyl-3-isopropylbenzene, and 39% (0.45 kg) of 1,2-dimethyl-3,5-diisopropylbenzene. Yield: 6.05 kg of 1,2-dimethyl-4-isopropylbenzene=85.03% of theory, relative to propene employed according to Example 1a).

2) Recyclization of the by-products from Example 1d)

The following were initially introduced into the reaction flask according to Example 1: 0.980 kg of o-xylene/nitromethane (89:11), 1.160 kg of distillation residue and 0.120 kg of a mixture of o-xylene/1,2-dimethyl-4-isopropylbenzene (63:36%). 4.220 kg of o-xylene, 0.057 kg of nitromethane and 0.120 kg of AlCl$_3$ were additionally added to the batch, so that the mixture was composed of: 5.167 kg of o-xylene, 0.165 kg of nitromethane, 0.120 kg of AlCl$_3$, 0.483 kg of 1,2-dimethyl-3-isopropylbenzene and 0.450 kg of 1,2-dimethyl-3,5-diisopropylbenzene.

The batch was isopropylated with 1.95 kg of propene according to Example 1a) and processed as described above. After filtration, 8.3 kg of a reaction mixture of the following composition were present: 1.6% nitromethane, 5.2% o-xylene, 81.1% 1,2-dimethyl-4-isopropylbenzene, 3.0% 1,2-dimethyl-3-isopropylbenzene, 9.1% 1,2-dimethyl-3,5-diisopropylbenzene.

3) One-step isopropylation of o-xylene

A 1 l flask (stirrer, gas inlet tube) was charged with 636 g of o-xylene and 16.5 g of nitromethane. 12 g of anhydrous aluminum chloride were added at 20° C. with stirring, and subsequently 2 g of hydrogen chloride and then, within the course of 2½ hours, 202 g of propene were passed in, the exothermic reaction being kept at a temperature of 90° C. Following the introduction of the propene, the reaction mixture was kept at 90° C. for a further period of time and the amounts of the components contained were determined at specific time intervals. The values in % by weight are given in the table.

|  | Total reaction time (hours) | | | | |
| --- | --- | --- | --- | --- | --- |
|  | 2½ | 4 | 6 | 8½ | 10½ |
| Nitromethane | 1.7 | 1.3 | 1.3 | 1.3 | 1.5 |
| o-xylene | 25.6 | 17.9 | 16.6 | 16.2 | 15.0 |
| 1,2,-dimethyl-4-isopropylbenzene | 44.7 | 74.2 | 76.9 | 78.3 | 78.5 |
| 1,2-dimethyl-3-isopropylbenzene | 5.3 | <1 | <1 | <1 | <0.5 |
| 1,2-dimethyl-3,5-diisopropylbenzene | 21.8 | 5.9 | 4.6 | 3.7 | 3.5 |
| 1,2-dimethyl-3,4,6-triisopropylbenzene | 0.5 | 0 | 0 | 0 | 0 |

Precipitation of the catalyst and further work-up were carried out as in the above examples.

4) Catalytic dehydrogenation of 1,2-dimethyl-4-isoproplbenzene 1 kg of 1,2-dimethyl-4-isopropylbenzene and 3 kg of water were fed in the course of an hour into an evaporator (about 300° C.) and subsequently heated to 590° C. by means of an electrically heated superheater. The mixture then flowed through a tubular reactor heated to 610° C., which contained 3 l of a tightly packed granular catalyst [type "Shell 105", composition Fe$_2$O$_3$ (87%) —KOH (11%) —Cr$_2$O$_3$ (2%), according to U.S. Pat. No. 2 461 147]. The contact time was 3.2 sec. The reaction mixture was strongly cooled with water in a condenser in which, at the same time, 40 g of a 0.5% strength aqueous solution of 4-tert-butyl-pyrocatechol per hour were added dropwise as an olefin stabilizer.

After separation of the phases, 0.95 kg of crude product was obtained.

The organic phase was treated with an additional 0.8 g of 4-tert-butylpyrocatechol and fractionally distilled at 10 mbar, 5.8% by weight of forerun, 24.9% by weight of 1,2-dimethyl-4-isopropylbenzene (b.p. 72° C./10 mbar), 68.2% by weight of 1,2-dimethyl-4-isopropenylbenzene (b.p. 76° C./10 mbar) and 1.1% by weight of higher-boiling constituents being obtained.

5) Addition of hydrogen chloride to 1,2-dimethyl-4-isopropenylbenzene

A 0.25 l flask with a stirrer following the wall and a gas inlet tube was filled with hydrogen chloride gas. 73 g of 1,2-dimethyl-4-isopropenylbenzene were then added drop-wise at −5° to −10° C. with vigorous stirring in the course of 30 minutes, hydrogen chloride being re-added. The absorption of gas was complete 5 minutes after the end of the dropwise addition. Hydrogen chloride was stripped off from the reaction product under reduced pressure (35° C./0.8 mbar) and 89.6 g (98.2% of theory) of 1,2-dimethyl-4-(α-chloroisopropyl)benzene were obtained, m.p.: −20° to −19° C., decomposition at >50° C./1 mbar with elimination of HCl.

Elemental analysis (C$_{11}$H$_{15}$Cl): found C 72.5%; H 8.15%; Cl 19.1%; calc.: C 72.31%; H 8.28%; Cl 19.41%;

6) Preparation of dixylylpropane

6a) Condensation of 1,2-dimethyl-4-(α-chloroisopropyl)benzene with o-xylene 106 g of o-xylene were initially introduced into a 0.5 l flask with a stirrer and gas inlet tube and saturated with hydrogen chloride gas at 0° C. 146 g of 1,2-dimethyl-4-isopropenylbenzene were then added dropwise in the course of 45 min with further introduction of hydrogen chloride gas and vigorous stirring. After the dropwise addition, hydrogen chloride gas was additionally passed in for a further 5 minutes (altogether about 38 g of hydrogen chloride). 424 g of o-xylene, 6.6 g of AlCl$_3$ and 9.1 g of CH$_3$NO$_2$ were saturated at −5° C. to 0° C. with hydrogen chloride gas in a 1 l flask with a stirrer and gas inlet tube. The solution of 1,2-dimethyl-4-(α-chloroisopropyl)benzene and o-xylene described above was then added dropwise in the course of 75 min with vigorous stirring to the hydrogen chloride gas-saturated o-xylene. The progress of the reaction was discernible by the vigorous evolution of gas.

The dissolved hydrogen chloride was expelled from the reaction solution at 0° C. with nitrogen. 13.4 g of finely divided calcium acetate × ½ H$_2$O were then added with stirring. The deposited precipitate was filtered off with suction and washed with 25 g of o-xylene.

The combined filtrates (705 g) were fractionally distilled. 360 g of o-xylene and nitromethane were obtained at normal pressure and 110°-145° C. The residual o-xylene (78 g) was removed by distillation at 20 mbar up to a head temperature of 45° C. Finally, dixylylpropane was distilled at 151° C./2.3 mbar. Yield: 232 g (92.3% of theory).

6b) Preparation of dixylylpropane from a mixture of 1,2-dimethyl-4-isopropenylbenzene and 1,2-dimethyl-4-isopropylbenzene A product mixture from the dehydrogenation according to Example 4 was distilled. In the course of this, a forerun was removed by distillation and the fraction 72°-76° C./10 mbar subsequently collected. 196.8 g of this fraction (contents: 25.8% by weight of 1,2-dimethyl-4-isopropylbenzene and 74.2% by weight of 1,2-dimethyl-4-isopropenylbenzene) contained 146 g of 1,2-dimethyl-4-isopropenylbenzene. This quantity was mixed at 0° C. with 106 g of o-xylene, reacted with HCl according to Example 6a and subsequently condensed at −5° to 0° C., 424 g of o-xylene, 6.6 g of AlCl₃ and 9.1 g of CH₃NO₂ being employed. After removal of the catalyst, the mixture was fractionally distilled. Dixylylpropane could be cleanly separated from o-xylene and 1,2-dimethyl-4-isopropylbenzene. Yield: 225.3 g (89.4% of theory) of dixylylpropane.

We claim:

1. A process for the preparation of dixylylpropane from o-xylene and propene, which comprises
   a) reacting o-xylene with propene in the presence of a Friedel-Crafts catalyst to give 1,2-dimethyl-4-isopropylbenzene,
   b) catalytically dehydrogenating 1,2-dimethyl-4-isopropylbenzene, to give 1,2-dimethyl-4-isopropenylbenzene,
   c) reacting a chlorinatable reactant comprising 1,2-dimethyl-4-isopropenylbenzene with hydrogen chloride to give 1,2-dimethyl-4α-chloroisopropyl)benzene and
   d) condensing a condensable reactant comprising 1,2-dimethyl-4-(α-chloroisopropyl) benzene with o-xylene to give dixylylpropane.

2. The process as claimed in claim 1, wherein the Fridel-Crafts catalyst comprises BF₃·H₃PO₄ or AlCl₃·CH₃NO₂.

3. The process as claimed in claim 1, wherein the reaction in said step a) is carried out at 60° to 130° C.

4. The process as claimed in claim 1, wherein the propene and o-xylene are reacted in a molar ration of 0.8 to 2.0.

5. The process as claimed in claim 2, wherein the AlCl₃ of said Fridel-Crafts catalyst is present in an amount of from 0.001 to 0.3 mol per mol of o-xylene.

6. The process as claimed in claim 2, wherein the AlCl₃ of the catalyst AlCl₃19 CH₃NO₂ is precipitated after the reaction of o-xylene with propene by addition of an alkali metal or alkaline earth metal acetate and is filtered off.

7. The process as claimed in claim 2, wherein the 1,2-dimethyl-4-isopropylbenzene, free of AlCl₃, obtained in step a), is fractionally distilled and the forerun and the residue are recycled to the reactor of step a) for renewed reaction.

8. The process as claimed in claim 1, wherein step b) is carried out in the presence of a catalyst comprising Fe₂O₃19 KOH·Cr₂O₃.

9. The process as claimed in claim 1, wherein, in step c), the hydrogen chloride is added at a temperature in the range of −30° to +40° C.

10. The process as claimed in claim 9, wherein said temperature is −10° to +10° C.

11. The process as claimed in claim 9, wherein, in step c), said chlorinatable reactant comprises a mixture of 1,2-dimethyl-4isopropylbenzene and 1,2-dimethyl-4-isopropenylbenzene.

12. The process as claimed in claim 1, wherein said condensable reactant comprises a mixture of 1,2-dimethyl-4-(α-chloroisopropyl)benzene and 1,2-dimethyl-4-isopropylbenzene.

13. The process as claimed in claim 12, wherein the reaction of step d) is carried out at −25° to +30° C.

14. The process as claimed in claim 12, wherein the reaction of step d) is carried out at −20° to 0° C.

* * * * *

UNITED STATES PATENT AND TRADEMARK OFFICE
CERTIFICATE OF CORRECTION

PATENT NO. : 5,300,717

DATED : April 5, 1994

INVENTOR(S) : Freimund Röhrscheid

It is certified that error appears in the above-indentified patent and that said Letters Patent is hereby corrected as shown below:

In the Abstract in the second to last line "modecule" should read -- molecule --.

At column 5, line 9 "(63:36%)" should read -- (64:36 %) --.

At column 5, lines 13-14 "1,2-dimethyl-3-isopropylbenzene" should read --1,2-dimethyl-4-isopropylbenzene--.

At column 5, line 14 insert after "isopropylbenzene" -- , 0.270 kg of 1,2-dimethyl-3-isopropylbenzene --.

In claim 2 at column 7, line 34 "Fridel-Crafts should read -- Friedel-Crafts --.

In claim 5 at column 8, line 5 "Fridel-Crafts" should read -- Friedel-Crafts --.

In claim 6 at column 8, line 8 "$AlCl_3 19CH_3NO_2$" should read -- $AlCl_3 \cdot CH_3NO_2$ --.

UNITED STATES PATENT AND TRADEMARK OFFICE
CERTIFICATE OF CORRECTION

PATENT NO. : 5,300,717
DATED : April 5, 1994
INVENTOR(S) : Freimund Röhrscheid

It is certified that error appears in the above-indentified patent and that said Letters Patent is hereby corrected as shown below:

In claim 8, at column 8, line 19 "$Fe_2O_3 19KOH \cdot Cr_2O_3$" should read

-- $Fe_2O_3 \cdot KOH \cdot Cr_2O_3$ --.

Signed and Sealed this

Fifteenth Day of November, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,300,717
DATED : April 5, 1994
INVENTOR(S) : Freimund Röhrscheid

It is certified that error appears in the above-identified patent and that said Letters Patent is hereby corrected as shown below:

Column 5, line 55, "isopropl benzene" should read --isopropylbenzene--.

Signed and Sealed this

Twenty-first Day of February, 1995

Attest:

BRUCE LEHMAN

Attesting Officer          Commissioner of Patents and Trademarks